US00PP10585P

United States Patent [19]

Hofmann

[11] Patent Number: Plant 10,585

[45] Date of Patent: Sep. 1, 1998

[54] VARIETY OF GERANIUM NAMED 'GLOBAL BRIGHT PURPLE'

[75] Inventor: Christa Hofmann, Grossdittmannsdorf, Germany

[73] Assignee: Elsner Pac Jungpflanzen, Germany

[21] Appl. No.: 744,433

[22] Filed: Nov. 8, 1996

[51] Int. Cl.[6] ..... A01H 5/00

[52] U.S. Cl. ..... Plt./87.12

[58] Field of Search ..... Plt./87.12

[56] References Cited

PUBLICATIONS

UPOV CD-ROM 97/03 Plant Breeders Rights to 'Purpalit' in four countries (DE, GB, HU, IL), 1994.

*Primary Examiner*—James R. Feyrer
*Assistant Examiner*—Melissa L. Kimball
*Attorney, Agent, or Firm*—Webb Ziesenheim Bruening Logsdon Orkin & Hanson, P.C.

[57] ABSTRACT

The new cultivar is an early, rich flowering variety. It produces elegant bright purple flowers continuously and early. It also has a cascading mound growth, improving shipping ability. The new cultivar is an improvement in comparison to the old purple variety "Cornell".

1 Drawing Sheet

BACKGROUND OF THE NEW PLANT

The present invention comprises a new and distinct cultivar of *Pelargonium×peltatum* known by the varietal name "Global Bright Purple" ("Purpalit" in Europe). The new cultivar was discovered at Elsner pac Jungpflanzen in Dresden, Germany, in 1990. The new variety was discovered in a controlled breeding program and bears the cross number 90K-2-18 where 90 refers to the year, K to Kreuzung (cross), 2 to a color group and 18 to the 18th selected individual of the progeny of this cross. Group pollination was employed. The new variety was first asexually reproduced by cuttings at Elsner pac Jungpflanzen in Dresden, Germany, in 1990 and at Oglevee, Ltd. in Connellsville, Pa., in January 1994. It has also been trial and field tested in Dresden, Germany and Connellsville, Pa. and has been found to retain its distinctive characteristics through successive propagations.

The plant history was taken on six-week plants blossomed under the natural light in a greenhouse in 10 cm pots. The cultivar when grown in a glass greenhouse was potted on Feb. 13, 1996 and flowered on Mar. 25, 1996.

DESCRIPTION OF THE DRAWING

The accomanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by Oglevee, Ltd. in Connellsville, Pa. The plant history was taken on six week plants blossomed under natural light in a greenhouse and the color readings were taken indoors under 200–220 footcandles of cool white fluorescent light. Color references are primarily to The R.H.S. Colour Chart of The Royal Horticultural Society of London.

The Plant

Classification:
- *Botanical.*—*Pelargonium×peltatum.*
- *Commercial.*—Ivy geranium.
- *Height.*—16.0–20.0 cm from soil level.

- *Growth.*—Cascading mound.
- *Foliage.*—Slightly reflective, slightly pubescent; stalked leaf attachment.

Leaves:
- *Size.*—5.5–7.5 cm.
- *Shape.*—Reniform, cordate base.
- *Margin.*—Pedately lobed.
- *Texture.*—Reflective, rough.
- *Color.*—Top: Green Group 137A. Bottom: Green Group 143C.
- *Zone.*—No prominent zone.

Ribs and veins:
- *Venation.*—Palmate.
- *Color.*—Yellow-Green Group 144A.

Petioles:
- *Color.*—Yellow-Green Group 144A.
- *Length.*—2.5–4.5 cm.

Stem:
- *Color.*—Yellow-Green Group 144A.
- *Internodes.*—2.5–6.0 cm in length.

The Bud (Umbel)

Shape: Elliptical cluster.
Size: 2.5 cm just breaking color.

Inflorescence

Blooming habit: Free and early flowering, continuous.
Size (diameter): 4.0 cm, fully open bloom.
- *Borne.*—Floret on pedicel, pedicel on peduncle, flowers 5.5–7.5 cm above the foliage.

Florets:
- *Bud size.*—1.0–1.5 cm.
- *Form.*—Ruffled, semi-double, cupped.
- *Color.*—Top: Outer edge is Red-Purple Group 74B with streaking of Red-Purple Group 72A. Bottom: Outer edge is Red-Purple Group 74A with veins that are white, creating a lighter overall color. Eye: Present only in some; often a Red-Purple Group 72A, other times a Red-Purple Group 79A.

Petals:
- *Quantity.*—23.
- *Size.*—2.5–3.5 cm across.
- *Texture and appearance.*—Smooth, velvety appearance, reflective.

Petaloids:
*Quantity.*—4–5.
*Shape.*—Irregular, twisted, ruffled.
*Color.*—Top: Red-Purple Group 74B. Bottom: Outer edge is Red-Purple Group 74A with some dark veins and white streaking.
Pedicel:
*Color.*—Yellow-Green Group 144A.
*Length.*—1.5–2.0 cm.
Peduncle:
*Color.*—Yellow-Green Group 144A.
*Length.*—15.0 cm.
Disease resistance: Not known.
Lasting quality: Shorter plant habit improves shipping ability.

Reproductive Organs

Stamens:
*Anthers.*—8.0 mm in length.
*Filaments.*—Length: 5.0–9.0 mm. Color: White with Purple tips.
*Pollen.*—Golden Brown.
Pistils:
*Number.*—5.
*Length.*—7.0 mm.
*Stigma.*—Color: Deep Purple.
*Style.*—Length: 2.0 mm.
Ovaries:
*Characteristic.*—Superior, pubescent.
*Length.*—2.0–3.0 mm.
*Color.*—Green.
Fruit: None observed.

General Characteristics

1. New rich, bright purple color, new to the ivy geranium class.

2. Compact mound growth.

3. Ease of rooting and finishing.

4. Shorter plant habit improves shipping ability.

5. Elegant flowers, big umbels and continuous flowering.

6. Free and early flowering.

7. Essential improvement in comparison to the old ivy geranium variety "Cornell" (unpatented) which is lighter in color.

I claim:

1. A new and distinct variety of geranium plant substantially as shown and described.

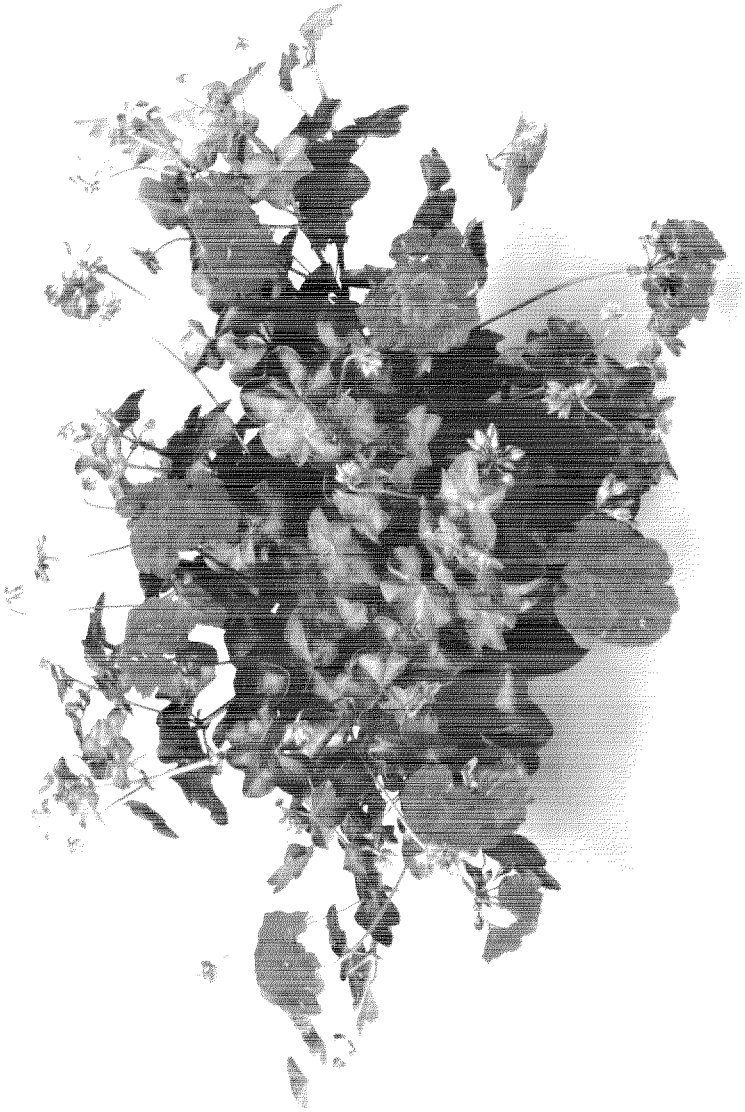

* * * * *